United States Patent

Günther et al.

[11] Patent Number: 5,681,474
[45] Date of Patent: Oct. 28, 1997

[54] LOW-PRESSURE CHROMATOGRAPHY COLUMN WITH AUTOMATICALLY MOVABLE LID

[75] Inventors: Joachim Günther, Kaiserslautern; Bernhard Krause, Frankfurt; Gernot Mader, Kelkheim; Wolfgang Sittig, Hofheim; Klaus Itter, Frankfurt; Klaus-Jürgen Simon, Kelkheim, all of Germany

[73] Assignee: Hoechst Aktiengesellschaft, Frankfurt, Germany

[21] Appl. No.: 522,616

[22] Filed: Sep. 1, 1995

[30] Foreign Application Priority Data

Sep. 6, 1994 [DE] Germany .................. 44 31 662.3

[51] Int. Cl.$^6$ ................................ B01D 15/08
[52] U.S. Cl. ............... 210/656; 210/91; 210/144; 210/198.2; 210/635
[58] Field of Search .................. 210/90, 91, 94, 210/95, 198.2, 635, 656, 143, 144; 422/70; 73/61.52, 61.53, 61.56, 61.57; 530/305; 96/101

[56] References Cited

U.S. PATENT DOCUMENTS

| | | | |
|---|---|---|---|
| 3,966,609 | 6/1976 | Godbille et al. | 210/198.2 |
| 4,891,133 | 1/1990 | Colvin | 210/198.2 |
| 5,324,426 | 6/1994 | Joseph et al. | 210/198.2 |
| 5,450,743 | 9/1995 | Buote | 210/198.2 |
| 5,462,659 | 10/1995 | Saxena et al. | 210/198.2 |

FOREIGN PATENT DOCUMENTS

| | | |
|---|---|---|
| 0008921 | 3/1980 | European Pat. Off. . |
| 0330503 | 8/1989 | European Pat. Off. . |
| 1767790 | 7/1971 | Germany . |

*Primary Examiner*—Joseph W. Drodge
*Attorney, Agent, or Firm*—Curtis, Morris & Safford, P.C.

[57] ABSTRACT

This invention relates to a low-pressure chromatography column 1 having a diameter of more than 30 cm, and essentially consisting of a vertical cylinder 13 having a base plate 12, a lower sintered disk 3 arranged above the base plate 12, an upper sintered disk 16 fastened to the underside of a lid designed as a mobile plunger 4, and having at least three controllable elements 5 for raising or lowering the plunger 4, which are connected to the plunger 4, equipped with sensors 6 electrically connected to a control unit 10 for determining the vertical position and horizontal placement of the plunger 4. With the aid of an optical observation device (e.g., endoscope), the plunger/gel material can be adjusted exactly over the entire positioning range of the plunger. The advantages of the invention include simple and rapid production of the packing and purer products than could be obtained without such packing. The low-pressure chromatography column according to the invention is particularly suitable for purifying insulin and precursors of insulin thereof.

11 Claims, 3 Drawing Sheets

LOW-PRESSURE CHROMATOGRAPHY COLUMN WITH AUTOMATICALLY MOVABLE LID

BACKGROUND OF THE INVENTION

The invention relates to a low-pressure chromatography column having a diameter of more than 30 cm. Low-pressure chromatography columns of the above-mentioned type are known. They essentially consist of a vertical cylinder, a base plate with an outlet, a lower sintered disk arranged above the base plate, an upper sintered disk and a lid with an inlet and designed as a mobile plunger, the upper sintered disk being fastened to the underside of this plunger.

Low-pressure chromatography columns of this type for pressures up to 10 bar are used, amongst other things, in methods for purifying human insulin and precursors thereof, in a plurality of procedural steps, the liquid phase to be purified flowing into the low-pressure chromatography column through the inlet, penetrating the upper sintered disk, on its way down being purified by a packing located between the lower and upper sintered disks and then leaving the low-pressure chromatography column through the lower sintered disk and the outlet.

SUMMARY OF THE INVENTION

In this case it is important for a good purification effect for the packing, which preferably consists of a gel material, to be included between the sintered disks homogeneously, firmly and as free as possible from bubble-type cavities (for example air inclusions). For proper production of such packing, the packing material is suspended in a liquid, and this suspension is applied onto the lower sintered disk through the low-pressure chromatography column which is open at the top. After the gel material has settled, the movable plunger is manually lowered in the chromatography column, in such a way that it is as horizontal as possible, with the aid of a hoisting device or a threaded rod, until the lower sintered disk touches the gel material. Additional liquid is thereupon applied, and this liquid flow leads to further compacting. The liquid is sucked out from below until the desired packing height is reached. This process is extremely time-consuming and extremely intensive in terms of work and labor, because with increasing column diameter, ie. internal diameter of the cylinder ≧30 cm, guiding of the plunger becomes ever poorer (tilting), which has a negative effect on the packing and on the operation of the column.

In addition, it is known from experiments with high-pressure chromatography columns, that the packing is formed nonhomogeneously if the above-described production lasts too long. The result is a poor purifying effect.

The invention provides a remedy for these disadvantages.

According to the invention, this is done in that the low-pressure chromatography column has controllable elements for raising or lowering the plunger, which are connected to the plunger, in that the controllable elements are equipped with sensors for determining the vertical position and horizontal placement of the plunger, and in that the sensors are electrically connected to a control unit for the controllable elements.

Further refinements of the invention are given in claims 2 to 7.

The invention is suitable for purifying insulin and precursors thereof.

The advantages which can be obtained using it are manifested, on the one hand, by simple and rapid production of the packing and, on the other hand, it has surprisingly been found that purer products can be obtained with such packing than hitherto.

An exemplary embodiment of the invention will be explained in more detail below with the aid of the drawing in FIGS. 1 to 3.

DESCRIPTION OF THE PREFERRED EMBODIMENTS

Figure 1:
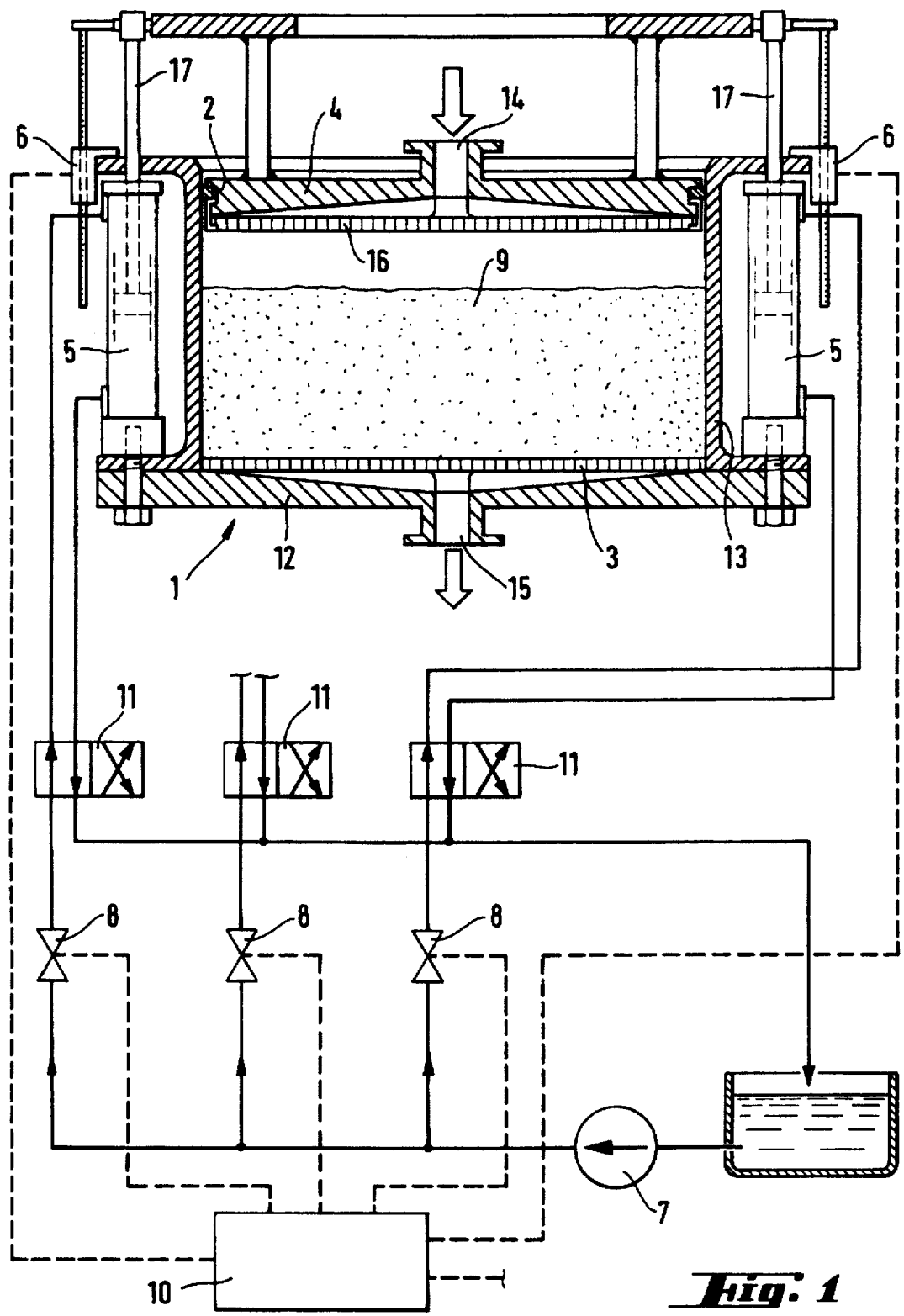
FIG. 1 shows a cross section through a low-pressure chromatography column with associated control unit and circuitry.

The low-pressure chromatography column 1 essentially consists of a vertical cylinder 13, a base plate 12 with outlet 15, a lower sintered disk 3 which is arranged directly above the base plate 12, and an upper sintered disk 16 which is fastened to the underside of a lid designed as a mobile plunger 4. The gap between the plunger 4 and the cylinder 13 is closed off by a seal 2. The plunger 4 is provided with an inlet 14.

Packing 9, preferably consisting of a gel, is located between the upper sintered disk 16 and the lower sintered disk 3 and is intended to be included firmly between the two sintered disks 16, 3, as homogeneously as possible and free of bubble-type cavities. In order to achieve this in the shortest possible time, a plurality, preferably three hydraulic cylinders 5 are externally fixed to the column, with the aid of which cylinders the plunger 4 can be moved vertically upward or downward via plunger rods 17 connected to the plunger 4, and optionally via a hydraulic unit 7 with controllable solenoid valves 8 and changeover valves 11.

For controlling the solenoid valves 8, use is made of a control unit 10, to the outputs of which the control valves 8 are connected.

The inputs of the control unit 10 are electrically connected to sensors 6 which are designed, in particular, as displacement sensors and one of which is respectively fixed to each plunger rod 17 of the hydraulic cylinder 5. With the aid of such sensors, the vertical position of the relevant plunger rod 17 is measured and transmitted to the control unit as an electrical signal. The set of positions of the individual plunger rods 17 characterize the vertical position and the horizontal placement of the plunger 4.

According to the position and placement of the plunger 4, the control unit 10 actuates the hydraulic cylinders 5 via the solenoid valves 8 in such a way that the plunger 4 is guided downward such that it is horizontal and at a preselectable speed. By actuation of the changeover valves 11, the plunger can be guided upward in a corresponding fashion. The changeover valve 11 is actuated manually, but automation of this process is possible.

In a further refinement of the invention, the lower instead of upper base plate 12 is designed as a mobile plunger and connected to elements 5 for raising or lowering the base plate 12.

Clearly, the plate and the lid can also be designed as mobile elements.

Figure 2:
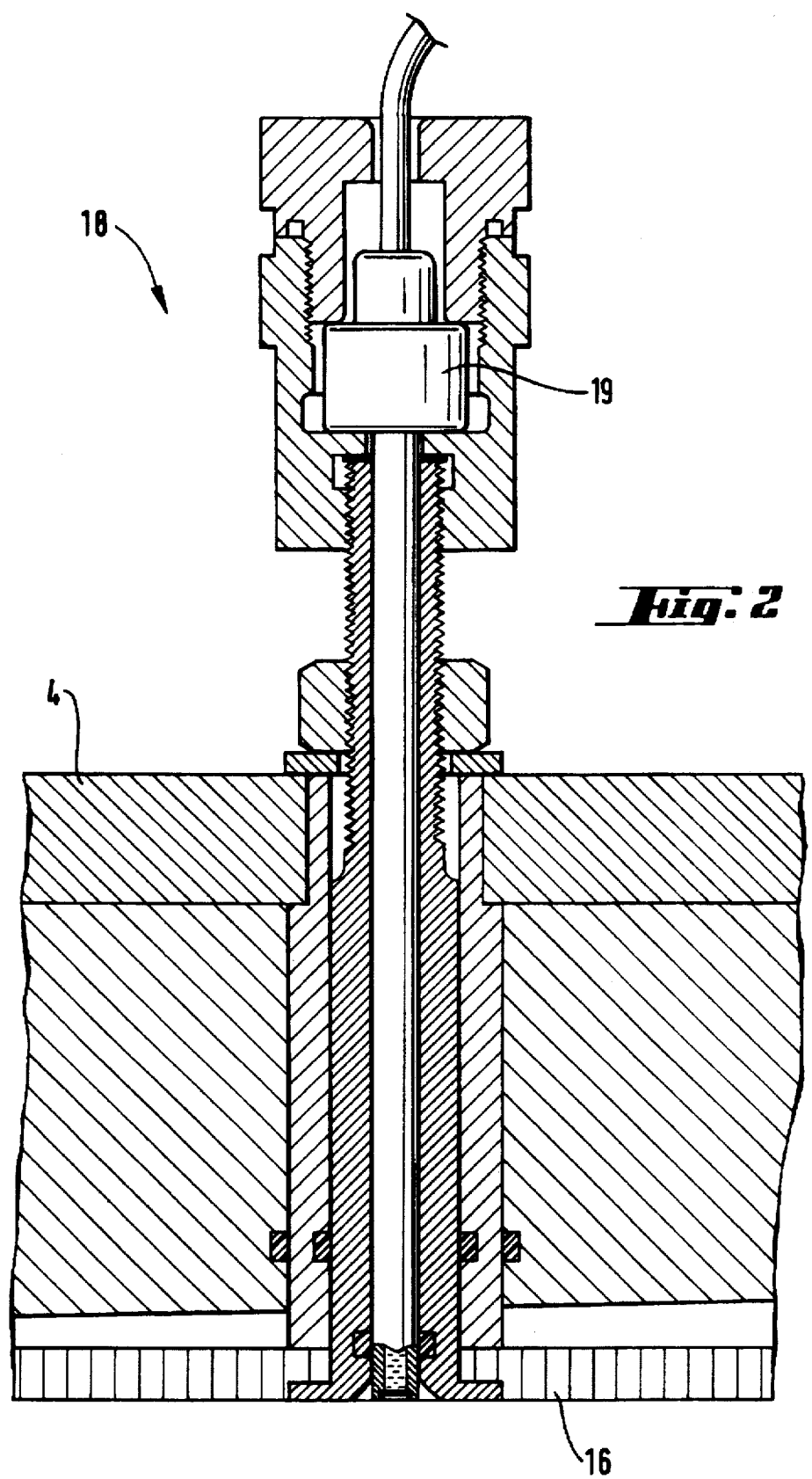
FIG. 2 shows a built-in pressure pick-up and FIG. 3 shows a built-in endoscope, respectively in cross section.

In a particular refinement, a pressure pick-up 18 with a cylindrical pressure sensor 19 (FIG. 2) is built into the plunger 4, and with its aid it is possible to measure the pressure directly above the gel material and forward it to the control unit 10.

Figure 3:
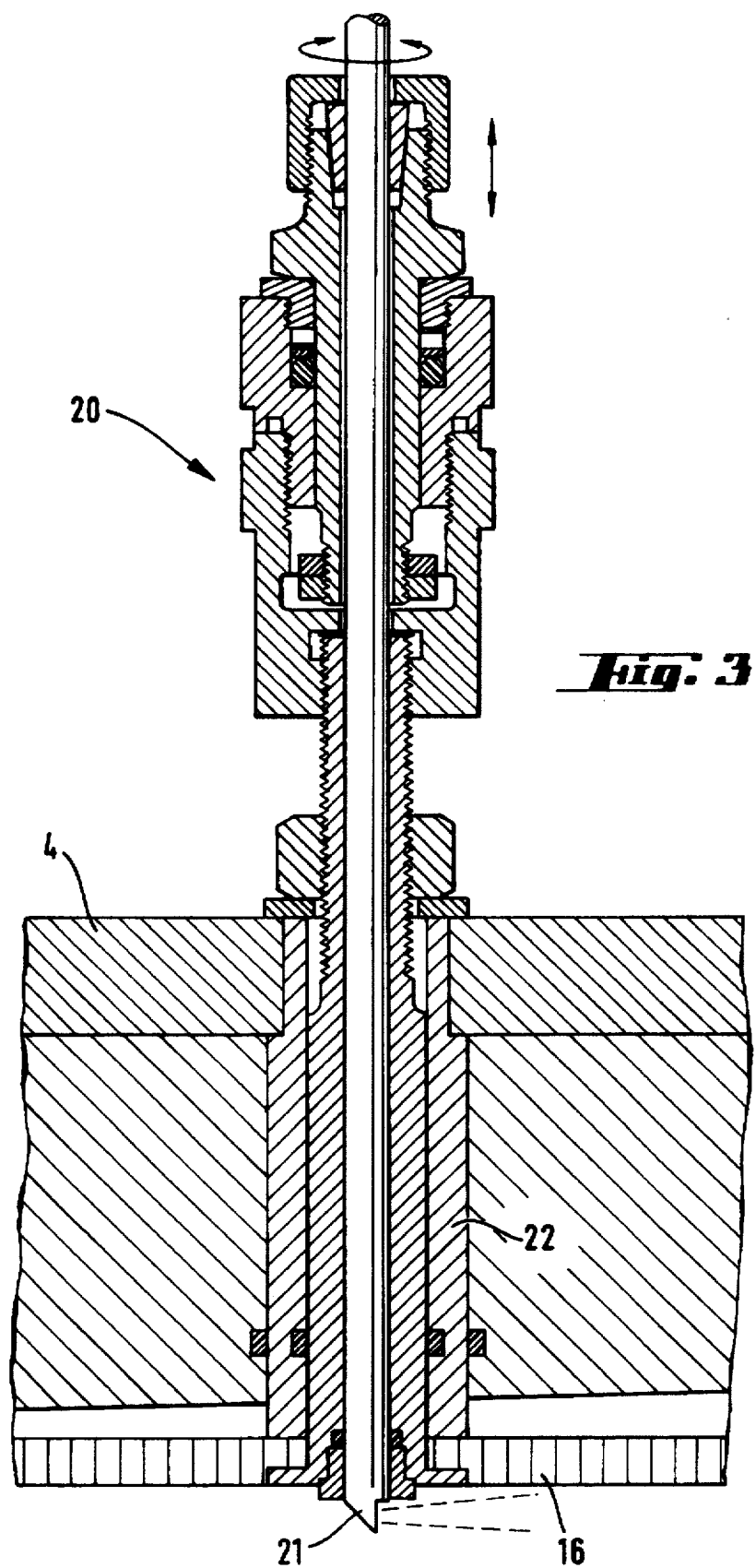

The internal diameter of the pressure sensor 19 terminates level with the surface of the sintered disk 16. The cross-sectional area should be kept as small as possible, in order not unnecessarily to reduce the area of the sintered disk 16 which is flowed through. It is further advantageous to equip the plunger 4 with an observation device 20, preferably with an endoscope 21 (FIG. 3), since this has the advantage that the entire positioning range of the plunger 4 can be monitored.

In addition, there are gel materials which "breathe" after the application of corresponding media. It is thus possible for the separation between the gel and the underside of the sintered disk to be examined or exactly adjusted even in the case of these gel materials.

In order to permit observation, the plunger 4 of the low-pressure chromatography column 1 is provided with a holder 22 which makes it possible for an endoscope 21 fitted immediately below the sintered disk 16 to be pivotable through 360° and adjustable in height. The endoscope 21 with 90° angular field makes it possible to adjust the separation between the gel material and the underside of the sintered disk exactly.

It is important in this case as well for the application flow to be not disturbed excessively by the small cross-sectional area of the endoscope holder.

We is claimed is:

1. A low-pressure chromatography column (1) having a diameter of more than 30 cm, essentially consisting of a vertical cylinder (13) having a base plate (12), a lower sintered disk (3) which is arranged above the base plate (12), an upper sintered disk (16) which is fastened to the underside of a lid designed as a mobile plunger (4), wherein the low-pressure chromatography column (1) has at least three controllable elements (5) for raising or lowering the plunger (4), which are connected to the plunger (4), wherein the controllable elements (5) are equipped with sensors (6) for determining the vertical position and horizontal placement of the plunger (4), and wherein the sensors (6) are electrically connected to a control unit (10) for the controllable elements (5).

2. The low-pressure chromatography column as claimed in claim 1, wherein the elements (5) for raising or lowering the plunger (4) are hydraulic cylinders.

3. The low-pressure chromatography column as claimed in claim 2, wherein the sensors (6) are displacement sensors.

4. The low-pressure chromatography column as claimed in claim 1, wherein the elements (5) for raising or lowering the plunger (4) are pneumatic cylinders.

5. The low-pressure chromatography column as claimed in claim 4, wherein the sensors (6) are displacement sensors.

6. The low-pressure chromatography column as claimed in claim 1, wherein the elements (5) for raising or lowering the plunger (4) are threaded spindles that can be operated by an electric motor.

7. The low-pressure chromatography column as claimed in claim 6, wherein the sensors (6) are displacement sensors.

8. The low-pressure chromatography column as claimed in claim 1, wherein the low-pressure chromatography column (1) is equipped with a pressure pick-up (18) for determining the pressure in the cylinder (13), and wherein the pressure pick-up (18) is electrically connected to the control unit (10).

9. The low-pressure chromatography column as claimed in claim 1, wherein the plunger (4) is equipped with an observation device (20).

10. A method of purifying complex organic compounds comprising introducing said complex organic compounds into a low-pressure chromatography column as claimed in claim 1.

11. A method of purifying insulin or precursors thereof comprising introducing said insulin or precursors thereof into a low pressure chromatography column as claimed in claim 1.

* * * * *